United States Patent
Ruh et al.

(10) Patent No.: US 9,404,859 B2
(45) Date of Patent: Aug. 2, 2016

(54) TUBE HANGERS AND SYSTEMS FOR VERY EARLY SMOKE DETECTION

(71) Applicant: The Boeing Company, Seal Beach, CA (US)

(72) Inventors: Anthony Charles Ruh, Seattle, WA (US); Jonathan Asher Schweiger, Seattle, WA (US); Michael Scott Engele, Kent, WA (US)

(73) Assignee: The Boeing Company, Chicago, IL (US)

( * ) Notice: Subject to any disclaimer, the term of this patent is extended or adjusted under 35 U.S.C. 154(b) by 193 days.

(21) Appl. No.: 14/147,930

(22) Filed: Jan. 6, 2014

(65) Prior Publication Data

US 2015/0192224 A1    Jul. 9, 2015

(51) Int. Cl.
*G01N 21/53*    (2006.01)
*F16L 3/13*    (2006.01)
*F16L 3/24*    (2006.01)

(52) U.S. Cl.
CPC . *G01N 21/53* (2013.01); *F16L 3/13* (2013.01); *F16L 3/24* (2013.01); *G01N 2201/0216* (2013.01)

(58) Field of Classification Search
None
See application file for complete search history.

(56) References Cited

U.S. PATENT DOCUMENTS

| | | | | |
|---|---|---|---|---|
| 3,376,003 A * | 4/1968 | Zimmermann | ............ | F16L 3/11 248/59 |
| 3,532,311 A * | 10/1970 | Havener | ................... | F16L 3/227 24/339 |
| 4,042,198 A * | 8/1977 | Takeuchi | ................. | E21F 17/02 248/62 |
| 4,119,285 A * | 10/1978 | Bisping | ..................... | F16L 3/24 248/222.12 |
| 5,018,260 A * | 5/1991 | Ziu | ........................... | F16L 7/00 138/108 |
| 2012/0133518 A1* | 5/2012 | Russwurm | ............. | G08B 29/18 340/628 |

* cited by examiner

*Primary Examiner* — Kara E Geisel
*Assistant Examiner* — Amanda Merlino
(74) *Attorney, Agent, or Firm* — DASCENZO Intellectual Property Law, P.C.

(57) ABSTRACT

Systems for very early smoke detection are disclosed, including details of tube hangers that may be used to hang sampling tubes for very early smoke detection systems. The systems and components thereof may be temporarily installed in aerospace vehicles during manufacturing. The tube hangers are generally compact, allowing use in confined spaces and/or near obstructions. Tube hangers comprise a support coupling mechanism, a tube clamp, and one or more suspension arms that span between the support coupling mechanism and the tube clamp. Tube hangers may be a unitary body that defines a tube clamp, one or more suspension arms, and a support coupling mechanism. Tube clamps define a tube clamp opening generally facing away from the support coupling mechanism.

20 Claims, 3 Drawing Sheets

TUBE HANGERS AND SYSTEMS FOR VERY EARLY SMOKE DETECTION

FIELD

The present disclosure relates to tube hangers and systems for very early smoke detection.

BACKGROUND

Very early smoke detection apparatuses use aspirating smoke detection to sense small amounts of smoke in an environment, typically far smaller amounts than can be noticed visually. Such very early smoke detection is useful in a variety of situations, especially where the environment is isolated, large, and/or contains high value assets. For example, very early smoke detection may be useful during the manufacture of large, complex apparatuses like aerospace vehicles. During manufacturing of aerospace vehicles, including during construction, repair, maintenance, retrofitting, and/or interior finishing, a very early smoke detection apparatus may be temporarily installed in the (at least partially assembled) aerospace vehicle.

Very early detection of nascent fires allows for the elimination of the hazard before significant injury and/or property damage. Very early smoke detection apparatuses detect smoke, and potentially other hazard indicators, by sampling the air in an environment. A very early smoke detection apparatus draws air from a range of sampling sites, optionally filters the air, and then, for smoke detection, measures remaining particulates by light scattering in a central monitoring device.

A very early smoke detection system includes a monitoring device and tubing (e.g., piping, conduit, ducting, and/or hose) distributed about the area to be protected. The tubing typically includes a series of sampling inlets that are configured to draw air from the local environment through the tubing to the monitoring device.

In an aerospace vehicle, the tubing, typically including flexible hose, may be distributed within the interior of the vehicle, with the tubing coupled to the vehicle interior with tube hangers. Conventional tube hangers typically are relatively bulky and complex. The bulk restricts placement of the tube hanger near corners, tight spaces, or other locations with low clearance. The complexity results in high cost of manufacture of the part and difficulty of operation (e.g., installation and removal). Conventional tube hangers include two parts that must be assembled by the user: (1) a base element with spring loaded jaws that clamp to an interior rail and (2) a breakaway hook that is configured to clamp a tube and to hook to the base element.

Hence, there is a need for tube hangers that may be placed throughout an aerospace vehicle interior and that are simple to manufacture and operate.

SUMMARY

Systems for very early smoke detection, and components thereof, are disclosed. Systems generally comprise a monitoring device, a sampling tube, and a tube hanger. The monitoring device is configured to sample air transported through the sampling tube. The tube hanger is coupled to a portion of the sampling tube and may be configured to couple the sampling tube to a support structure.

A tube hanger, which may be configured for a very early smoke detection system, may comprise a support coupling mechanism, a tube clamp, and one or more suspension arms spanning between the support coupling mechanism and the tube clamp. The tube clamp defines an opening facing away from the support coupling mechanism. The tube hanger may be a unitary body and may be formed into a band. The unitary body and/or band may define at least one of the support coupling mechanism, the tube clamp, and the suspension arms.

The tube hanger may comprise at least two suspension arms which may be substantially symmetrically disposed about a central axis of the tube hanger. The central axis runs from the center of the support coupling mechanism to the center of the opening of the tube clamp. The suspension arms generally have an arcuate profile. The tube clamp may have a C-shape profile and the tube clamp in conjunction with two suspension arms may have an omegoid profile.

The tube hanger may be configured to apply a grip force through the support mechanism. The support coupling mechanism may include one or more coupling elements. When including a plurality of coupling elements, the plurality of coupling elements may be configured to cooperate to couple the tube hanger to a mating support such as a portion of an aircraft during manufacturing.

The tube hanger may be configured to retain a sampling tube with the tube clamp. The tube clamp may be configured to accept a sampling tube with low insertion force and may be configured to release the sampling tube upon application of a force directed away from the support coupling mechanism. The tube clamp may be configured to accept and to retain a sampling tube after release of the sampling tube due to a force directed away from the support coupling mechanism.

DESCRIPTION

Figure 1:
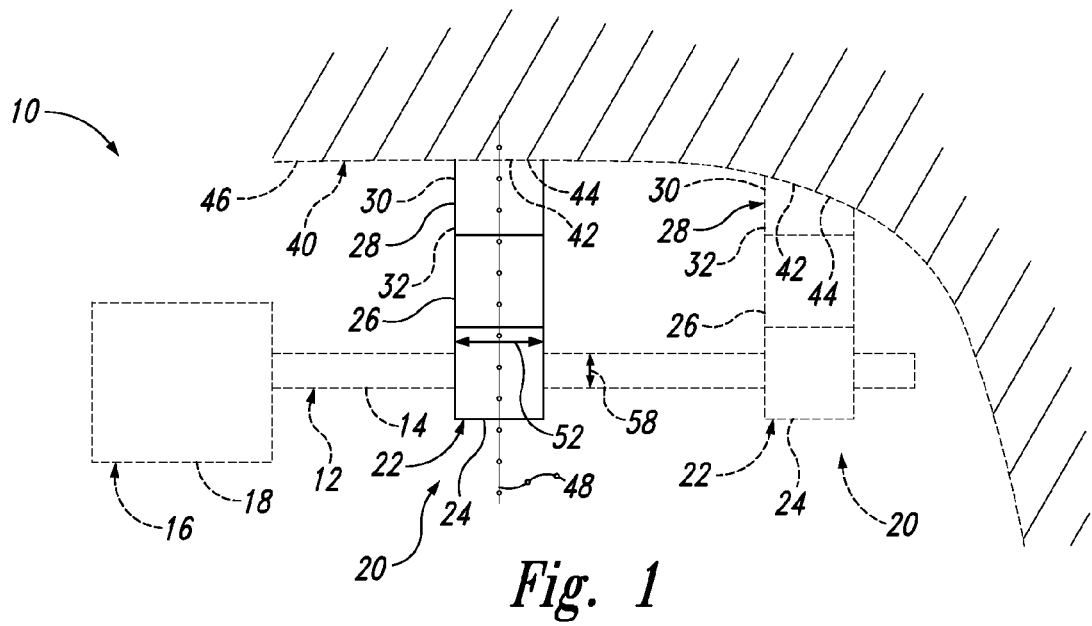
FIG. 1 is a schematic representation of very early smoke detection systems and tube hangers.

FIGS. 1-5 illustrate various embodiments of systems 10 for very early smoke detection and/or tube hangers 20. Elements that serve a similar, or at least substantially similar, purpose are labeled with numbers consistent among the figures. Like numbers in each of FIGS. 1-5, and the corresponding elements, may not be discussed in detail herein with reference to each of FIGS. 1-5. Similarly, all elements may not be labeled in each of FIGS. 1-5, but reference numerals associated therewith may be used for consistency. Elements, components, and/or features that are discussed with reference to one or more of FIGS. 1-5 may be included in and/or used with any of FIGS. 1-5 without departing from the scope of the present disclosure. In general, elements that are likely to be included are illustrated in solid lines, while elements that may be optional or alternatives are illustrated in dashed lines. However, elements that are shown in solid lines are not necessarily essential, and an element shown in solid lines may be omitted without departing from the scope of the present disclosure.

FIG. 1 is a schematic representation of systems 10 for very early smoke detection. Systems 10 comprise a monitoring device 16, one or more sampling tubes 12, and one or more tube hangers 20. Generally, systems 10 are configured to detect smoke from an environment by aspirating air samples through a sampling tube 12 and delivering those air samples to the monitoring device 16 where smoke may be detected. Tube hangers 20 are configured to couple sampling tubes 12 to support structures 40, structures that are within, or at least partially define, a monitored region of the environment. Support structures 40 may be a portion of an aerospace vehicle (e.g., a portion of an aircraft interior such as an overhead rail in an aircraft cabin). Sampling tubes 12 in systems 10 are arranged to sample air generally throughout the monitored region. Systems 10 may be configured for use during manufacture of aerospace vehicles, including during construction, repair, maintenance, retrofitting, and/or interior finishing. Systems 10 may be configured for temporary installation. For example, systems 10 may be configured for installation in an aircraft during interior finishing and for removal from the aircraft after completion of manufacture.

Systems 10 for very early smoke detection include a sampling tube 12, typically a network of sampling tubes 12, with at least one sampling inlet 14 to sample the neighboring environment. The sampling tubes 12 are configured to sample air and deliver the air to a monitoring device 16. The sampling tubes 12 may include, and optionally may be, pipe, conduit, ductwork, and/or hose. Further, the sampling tubes 12 may include at least a portion that is flexible or rigid. Sampling tubes 12 may be characterized by an outer diameter 58. The outer diameter 58 is the effective diameter of the outer profile of the sampling tube 12 (i.e., sampling tubes 12 need not have a circular profile). The outer diameter 58 may be greater than 6 mm, greater than 8 mm, greater than 10 mm, greater than 12 mm, greater than 16 mm, greater than 20 mm, greater than 24 mm, greater than 28 mm, greater than 32 mm, greater than 40 mm, greater than 50 mm, less than 100 mm, less than 80 mm, less than 70 mm, less than 60 mm, less than 50 mm, less than 40 mm, less than 32 mm, less than 28 mm, less than 24 mm, less than 20 mm, 6-100 mm, 6-60 mm, and/or 12-40 mm.

Systems 10 for very early smoke detection include a monitoring device 16. The monitoring device 16 generally is configured to detect the presence of smoke in the air samples delivered to the monitoring device 16. Additionally or alternatively, the monitoring device 16 may detect other properties of the sampled air, for example, temperature, moisture, and/or hazardous gases. Generally, the monitoring device 16 is configured to detect smoke by measuring light scattering (the presence of smoke causes light to scatter as light is transmitted through a sample of air). The monitoring device 16 may be configured to draw air through the sampling tube 12, and thereby aspirate samples of air from the environment. Additionally or alternatively, systems 10 may include a suction device 18 that is configured to draw air through the sampling tube 12 and to transport a portion of the air to the monitoring device 16.

Systems 10 for very early smoke detection include one or more tube hangers 20, each configured to couple a portion of the sampling tube 12 to a support structure 40. Tube hangers 20 comprise a support coupling mechanism 28, a tube clamp 22 defining a tube clamp opening 24, and one or more suspension arms 26 spanning between the support coupling mechanism 28 and the tube clamp 22. Generally, tube hangers 20 are configured for at least temporary coupling to the support structure 40, i.e., the tube hanger 20 is configured to be coupled to and uncoupled from (e.g., inserted into and removed from) the support structure 40. Tube hangers 20 may be configured to be coupled to and uncoupled from support structures 40 repeatedly, optionally without significantly damaging the support structure 40 and/or the tube hanger 20.

Generally, tube hangers 20 are configured for use in an enclosed space (e.g., within an aerospace vehicle). Therefore, tube hangers 20 generally are configured to avoid harm to personnel, equipment and the enclosed space. Tube hangers 20 may be light weight, compact, non-marring, and/or smooth. For example, tube hangers 20 may be configured to avoid injury and/or damage if the tube hanger 20 is dropped and/or dislodged from a support structure 40. As another example, tube hangers 20 may be constructed with no snags, protrusions, and/or sharp edges that would likely harm a support structure 40, a person, and/or equipment.

Generally, tube hangers 20 are configured to hang vertically, at least substantially non-horizontally, with the support coupling mechanism 28 above the tube clamp 22 and with the tube clamp opening 24 facing downward. However, tube hangers 20 are not restricted to hanging vertically; tube hangers 20 may hang at any angle. For example, tube hangers 20 may hang, or project, from a support structure 40 substantially horizontally. When installed, tube hangers 20 may retain a sampling tube 12 below the support structure 40. Where a tube hanger 20 is configured to project from a support structure 40 at an angle from vertical, the tube clamp opening 24 may face substantially downward.

Tube hangers 20 may be compact enough to fit within confined spaces and/or avoid interference with personnel and equipment. Generally, tube hangers 20 may be compact enough to retain the sampling tube 12 near obstructions. In aerospace vehicles, the interior space may include obstructed regions such as corners and highly sloped ceilings. Generally, a compact tube hanger 20 has a spatial extent comparable to the outer diameter 58 of the sampling tube 12. For example, a tube hanger 20 may have a relatively narrow depth 52, having a depth 52 that is about the same as or less than the outer diameter 58 of the sampling tube 12. The depth 52 is the maximum spatial extent of a tube hanger 20 in a direction generally parallel to the air flow direction of the sampling tube 12 (i.e., perpendicular to the outer diameter 58 of the sampling tube 12). Tube hangers 20 may have a depth 52 that is substantially uniform and/or that is less than 100 mm, less than 80 mm, less than 60 mm, less than 50 mm, less than 40 mm, less than 32 mm, less than 28 mm, less than 24 mm, less than 20 mm, less than 16 mm, less than 12 mm, less than 10 mm, 10-100 mm, and/or 12-40 mm.

Figure 2:
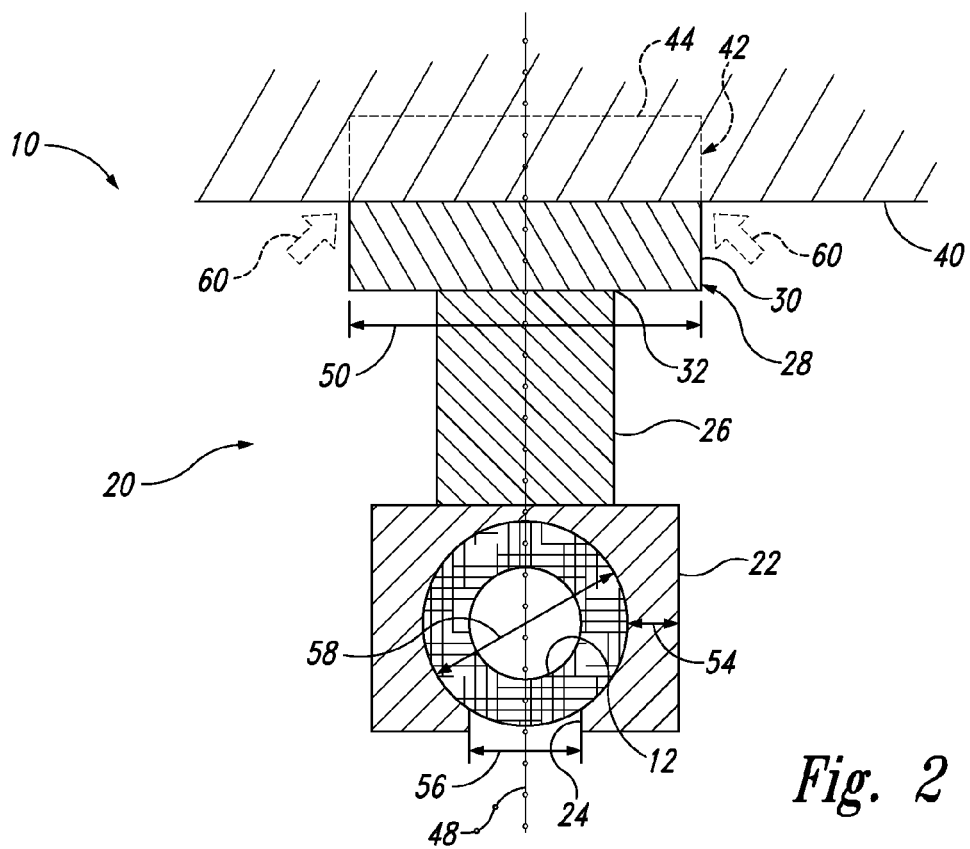
FIG. 2 is a schematic cross-sectional view of tube hangers within very early smoke detection systems.

Further, as viewed in FIG. 2, tube hangers 20 may have a relatively narrow width 50, having a width 50 that is about the same as, or not considerably larger (at least not significantly larger) than, the outer diameter 58 of the sampling tube 12. The width 50 is the maximum spatial extent of a tube hanger 20 in a direction generally perpendicular to the air flow direction of the sampling tube 12 and generally perpendicular to a central axis 48 passing through the tube clamp 22 and the support coupling mechanism 28. For example, the width 50 may be less than 5 times the outer diameter 58, less than 4 times the outer diameter 58, less than 3 times the outer diameter 58, less than 2.5 times the outer diameter 58, less than 2 times the outer diameter 58, less than 1.5 times the outer diameter 58, less than 1.2 times the outer diameter 58, less than 1.1 times the outer diameter 58, and/or 1.1-5 times the outer diameter 58. The width 50 may be less than 200 mm, less than 150 mm, less than 100 mm, less than 80 mm, less than 60 mm, less than 50 mm, less than 40 mm, less than 32 mm, less than 28 mm, less than 24 mm, 20-200 mm, and/or 40-100 mm.

Tube hangers 20 generally are constructed of materials selected for environmental resistance (e.g., exposure to temperature extremes, chemical solvents, and/or electrical hazards), durability, and flexibility (including elastic characteristics). Tube hangers 20 and components thereof (e.g., tube clamps 22, suspension arms 26, and support coupling mechanisms 28) may include spring elements and/or have spring characteristics. Tube hangers 20 may include at least one of a polymer, a plastic, and a metal, and may include a durable, smooth finish. Tube hangers 20 may be essentially composed of at least one of a polymer, a plastic and a metal. Suitable materials include nylon, ABS plastic (acrylonitrile butadiene styrene), steel, iron alloys, and copper alloys. Tube hangers 20 may include a soft, durable outer coating, e.g., the outer coating may be non-marring, elastic, conformable, and/or impact absorbing.

As viewed in FIG. 2, tube hangers 20 comprise a support coupling mechanism 28, a tube clamp 22, and one or more suspension arms 26 spanning between the support coupling mechanism 28 and the tube clamp 22. Though comprising these three elements, tube hangers 20 may be a unitary body, i.e., a one-piece structure. A one-piece design may simplify installation (by not requiring alignment, attachment, and/or adjustment of multiple parts). Likewise, a one-piece design may simplify removal of the tube hanger 20, and engagement and/or disengagement of a sampling tube 12. A unitary body may be formed by stamping, folding, rolling, forming, molding, extruding, machining, and/or additive manufacturing. The tube hanger 20 may be formed of a band, or formed into a band, which may be bent, folded, extruded, stamped, cut, and/or molded to define one or more of the support coupling mechanism 28, the tube clamp 22, and the one or more suspension arms 26. A band may be characterized as an elongated, thin strip, optionally having a substantially uniform cross section. The tube hanger 20 may have a thickness 54, the width of the material of the tube hanger 20 in a cross section parallel to the outer diameter 58 of the sampling tube 12 (i.e., a cross section perpendicular to the depth 52). The thickness 54 may be substantially uniform for the unitary body, the tube clamp 22, the one or more suspension arms 26, and/or the support coupling mechanism 28. The thickness 54 may be less than 20 mm, less than 15 mm, less than 12 mm, less than 10 mm, less than 8 mm, less than 6 mm, less than 4 mm, less than 2 mm, less than 1 mm, 1-20 mm, and/or 2-6 mm.

Tube hangers 20 may be visually distinct and may including tags, symbols, and/or coloration that are configured to make the device readily identifiable. Visual indications aid inspection of installation and removal of the tube hangers 20, and aid worker safety as well. Where the tube hangers 20 may hang near equipment and/or personnel, the visual indication serves as a ready warning of the presence of the tube hanger 20. Hence, personnel are apt to avoid hitting themselves or equipment against the tube hanger 20. Tube hangers 20 may be visually distinct if distinctively colored, contrasting with nearby structures, striped, fluorescent, luminescent, luminous, and/or brightly colored (e.g., bright red, bright pink, bright yellow, bright green, bright blue, etc.).

Tube hangers 20 comprise a tube clamp 22 that defines a tube clamp opening 24 facing away from the support coupling mechanism 28. Tube clamps 22 may be configured to accept and to retain a sampling tube 12. Tube hangers 20 may be configured to accept and to retain a sampling tube 12 with the tube clamp 22.

Generally, tube clamps 22 are configured to accept a sampling tube 12 through the tube clamp opening 24. Generally, a sampling tube 12 may be inserted into the tube clamp 22 laterally (along the tubing elongate direction) and/or transversely (generally perpendicularly to the tubing elongate direction) through the tube clamp opening 24. When a sampling tube 12 is inserted, the tube clamp 22 generally elastically flexes, stretches, and/or expands to accommodate the sampling tube 12. Insertion typically involves a friction fit between the sampling tube 12 and the tube clamp 22. Tube clamps 22 may be configured to accept a sampling tube 12 by hand operation (without tools), e.g., requiring low insertion force (0-50 N, 0-11 lbs.).

Generally, tube clamps 22 are biased to retain a sampling tube 12, potentially by applying forces to the sampling tube 12 and/or by maintaining a tube clamp opening 24 that is less than the outer diameter 58 of the sampling tube 12. Tube clamps 22 generally are configured to conform to the sampling tube 12, and may be configured to contact the majority of the circumference of the sampling tube 12. For example, a tube clamp 22 may have a C-shaped profile and may be configured to contact the circumference of the sampling tube 12 except in the region of the tube clamp opening 24. The contact may be a friction fit. Alternatively, tube clamps 22 may be configured to retain a sampling tube 12 with a loose fit. For example, a tube clamp 22 may be configured to contact the circumference of the sampling tube 12 only near the tube clamp opening 24.

The tube clamp opening 24 is an opening facing away from the support coupling mechanism 28, and generally facing away from the support structure 40 (when the tube hanger 20 is installed). Generally, the tube clamp opening 24 spans the depth 52 of the tube clamp 22. Hence, the tube clamp opening 24 may be described as an opening, an aperture, a gap, a slit, a slot, and/or a cleft. The opening width 56 of the tube clamp opening 24 may be less than 95%, less than 90%, less than 80%, less than 70%, less than 60%, less than 50%, and/or 50-95% of the outer diameter 58 of the sampling tube 12. The opening width 56 may be greater than 3 mm, greater than 4 mm, greater than 5 mm, greater than 6 mm, greater than 8 mm, greater than 10 mm, greater than 12 mm, greater than 16 mm, greater than 20 mm, greater than 24 mm, greater than 28 mm, greater than 32 mm, greater than 40 mm, greater than 50 mm, less than 100 mm, less than 80 mm, less than 70 mm, less than 60 mm, less than 50 mm, less than 40 mm, less than 32 mm, less than 28 mm, less than 24 mm, less than 20 mm, 3-100 mm, 6-60 mm, and/or 12-40 mm.

Tube hangers 20 generally are configured to securely hold a sampling tube 12 in normal operation and to release the sampling tube 12 if subject to a force greater than a predetermined threshold. For example, tube hangers 20 may be configured to release the sampling tube 12 if subject to forces corresponding to accidental tugging of the sampling tube 12 (e.g., due to entanglement with personnel and/or equipment).

Tube hangers 20 and/or tube clamps 22 may be configured to retain a sampling tube 12 while the force directed away from the support structure 40 (including the weight of the sampling tube 12) is less than 10 N (2 lbs.), 20 N (4 lbs.), 30 N (7 lbs.), 40 N (9 lbs.), and/or less than 50 N (11 lbs.). Tube clamps 22 may be configured to release the sampling tube 12 when the force directed away from the support structure 40 (e.g., the downward force) exceeds 20 N (4 lbs.), 30 N (7 lbs.), 40 N (9 lbs.), 50 N (11 lbs.) and/or or 60 N (13 lbs.).

Tube hangers 20 and/or tube clamps 22 may be configured to release the sampling tube 12 by breaking, deforming and/or stretching (permanently or temporarily). Tube clamp 22 may be configured to repeatedly engage and disengage a sampling tube 12, including when the sampling tube 12 is pulled away from the tube clamp 22 by accident. When the sampling tube 12 is removed from the tube hanger 20 by accident, the tube hanger 20 may be reusable and/or resettable (i.e., the release occurs without significant damage to the tube clamp 22 and/or the tube hanger 20).

Tube hangers 20 may be configured to hold a sampling tube 12 spaced away from a support structure 40. Holding the sampling tube 12 away from the support structure 40 may provide access to the support structure 40 near the sampling tube 12 and/or may allow the system 10 to better sample the environment (e.g., by providing air access around the sampling tube 12). Tube hangers 20 may be configured to separate the sampling tube 12 from the support structure 40 by greater than 20 mm, greater than 40 mm, greater than 60 mm, greater than 80 mm, greater than 100 mm, less than 150 mm, less than 100 mm, and/or 20-150 mm.

Tube hangers 20 comprise one or more suspension arms 26 spanning between the support coupling mechanism 28 and the tube clamp 22. For example, a tube hanger 20 may comprise at least two suspension arms 26. Generally, each suspension arm 26 is flexible and/or arcuate. Suspension arms 26 may form an elastic spring between the tube clamp 22 and the support coupling mechanism 28. The suspension arms 26 generally are disposed substantially symmetrically about the central axis 48 of the tube hanger, e.g., where a tube hanger 20 includes two suspension arms 26, one arm is on either side of the central axis 48. The central axis 48 of the tube hanger 20 is an axis running from the center of the support coupling mechanism 28 to the center of the tube clamp opening 24, generally through the center of the tube clamp 22, and generally through the air flow through a sampling tube 12 held by the tube clamp 22. Where a tube hanger 20 comprises two suspension arms 26, each suspension arm 26 may be connected to the tube clamp 22 at a different side of the tube clamp opening 24, optionally forming an omegoid profile.

Tube hangers 20 comprise a support coupling mechanism 28. The support coupling mechanism 28 is configured to couple the tube hanger 20 to the support structure 40, generally by applying a grip force 60. Tube hangers 20 may be configured to apply a grip force 60 through the support coupling mechanism 28. Though grip forces 60 are illustrated as directed towards the central axis 48, each grip force 60 independently may be applied in a different direction, i.e., each grip force 60 may be independently directed. For example, all grip forces 60 may be directed towards the central axis 48 or away from the central axis 48. As another example, at least one grip force 60 may be directed towards the central axis 48.

The support coupling mechanism 28 may be configured to couple to the support structure 40 even when the support structure 40 includes no features uniquely configured to couple to a tube hanger 20. The support coupling mechanism 28 may be biased to apply a grip force 60 to grip a mating support 42 (a portion of the support structure 40 that a tube hanger 20 is configured to be coupled to). Additionally or alternatively, the mating support 42 may be adapted to apply a force to a mating structure such as the support coupling mechanism 28. The mating support 42 may include, and optionally may be, a rail, a rib, a flange, ducting, and/or an air outlet. Support coupling mechanism 28 may be configured to couple to a range of sizes of mating supports 42, for example to a mating support 42 with a width between 20-200 mm, 20-100 mm, and/or 40-80 mm.

Generally, support coupling mechanisms 28 are configured for at least temporary coupling to the mating support 42, i.e., the support coupling mechanism 28 is configured to be coupled to and uncoupled from the mating support 42. Support coupling mechanisms 28 may be configured for repeated coupling to and/or uncoupling from the mating support 42, optionally without significantly damaging the mating support 42, the support structure 40, the support coupling mechanism 28, and/or the tube hanger 20.

A support coupling mechanism 28 may be configured to hold the tube hanger 20 to the support structure 40 rigidly and/or elastically. The support coupling mechanism 28 may be configured to retain the tube hanger 20 to the support structure 40 while the load due to the sampling tube 12 and/or any applied forces is less than 100 N (22 lbs.), less than 80 N (18 lbs.), less than 60 N (13 lbs.), less than 50 N (11 lbs.), less than 40 N (9 lbs.), less than 30 N (7 lbs.), and/or less than 20 N (4 lbs.).

Support coupling mechanisms 28 may include at least one coupling element 30. Coupling elements 30 may be at the tip 32 of a suspension arm 26, optionally extending from the tip 32. Each suspension arm 26 may include at least one coupling element 30 and each coupling element 30 may be of the same type. Coupling elements 30 may be male, female, and/or include male and/or female components. For example, coupling elements 30 may include at least one of a projection, a hook, a protrusion, a barb, a prong, a stud, a boss, a receptacle, a slot, a socket, and an adhesive. Support coupling mechanisms 28 may include a plurality of coupling elements 30 which may be configured to cooperate to couple the tube hanger 20 to a mating support 42. Each coupling element 30 independently may face the central axis 48. For example, at least one, optionally all, coupling element 30 may face towards the central axis 48. As another example, at least one, optionally all, coupling element 30 may face away from the central axis 48.

Further aspects of inventive subject matter are illustrated without limitation in the following illustrative, non-exclusive examples. These examples are included for illustration and are not intended to limit or define the entire scope of the present teachings.

Figure 3:
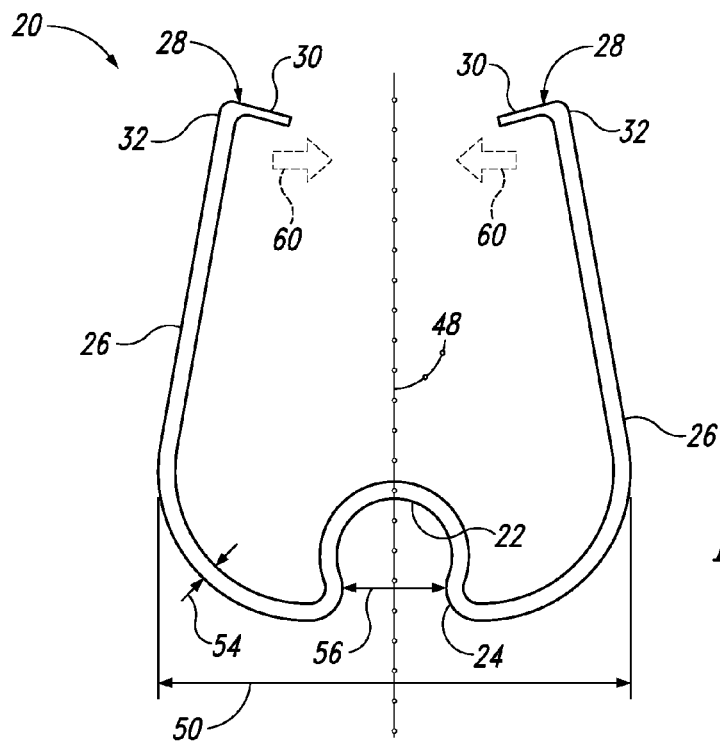
FIG. 3 is a profile view of an illustrative, non-exclusive example of a tube hanger.

FIG. 3 is profile view of an illustrative, non-exclusive example of a tube hanger 20. This tube hanger 20 comprises a C-shaped tube clamp 22, two arcuate suspension arms 26, and a support coupling mechanism 28 that includes a coupling element 30 at the tip 32 of each suspension arm 26. The tube hanger 20 is a unitary body, generally formed of a resilient plastic which allows the suspension arms to flex sideways (towards and away from the central axis in this profile view). The tube hanger 20 is formed into a band with a generally uniform thickness 54. The tube clamp 22 and the suspension arms 26 form an omegoid shape.

Generally, the tube hanger 20 is configured to retain a sampling tube 12 below a support structure 40, with the tube clamp opening 24 configured to face downward. The tube hanger 20 is configured to apply a grip force 60 with the support coupling mechanism 28, including the coupling elements 30. The grip force 60 is configured to be directed toward the central axis 48. The coupling elements 30 are of the same type and are each a thin, flat projection facing towards the central axis 48. The coupling elements 30, and the support coupling mechanism 28 generally, are configured to couple a mating support 42 which includes a lateral flange.

Figure 4:
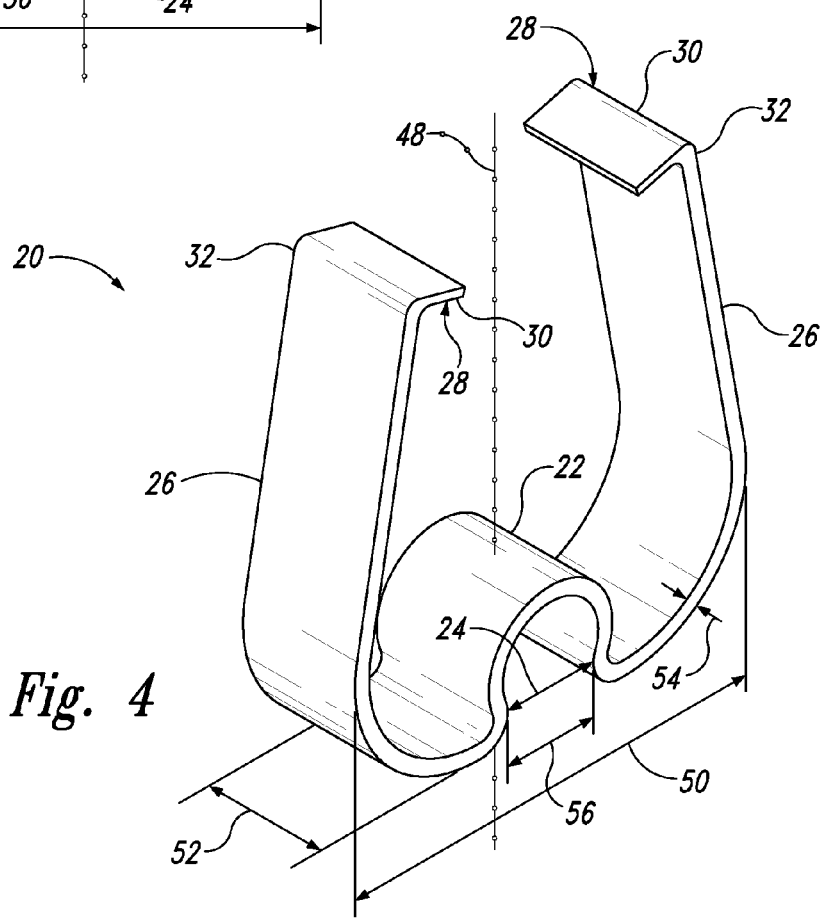
FIG. 4 is a perspective view of the illustrative, non-exclusive example tube hanger of FIG. 3.

FIG. 4 is a perspective view of the tube hanger 20 of FIG. 3. In this view, the relationships of the dimensions (the width 50, the depth 52, the thickness 54 and the opening width 56 of the tube clamp opening 24) are more clearly visualized.

Figure 5:
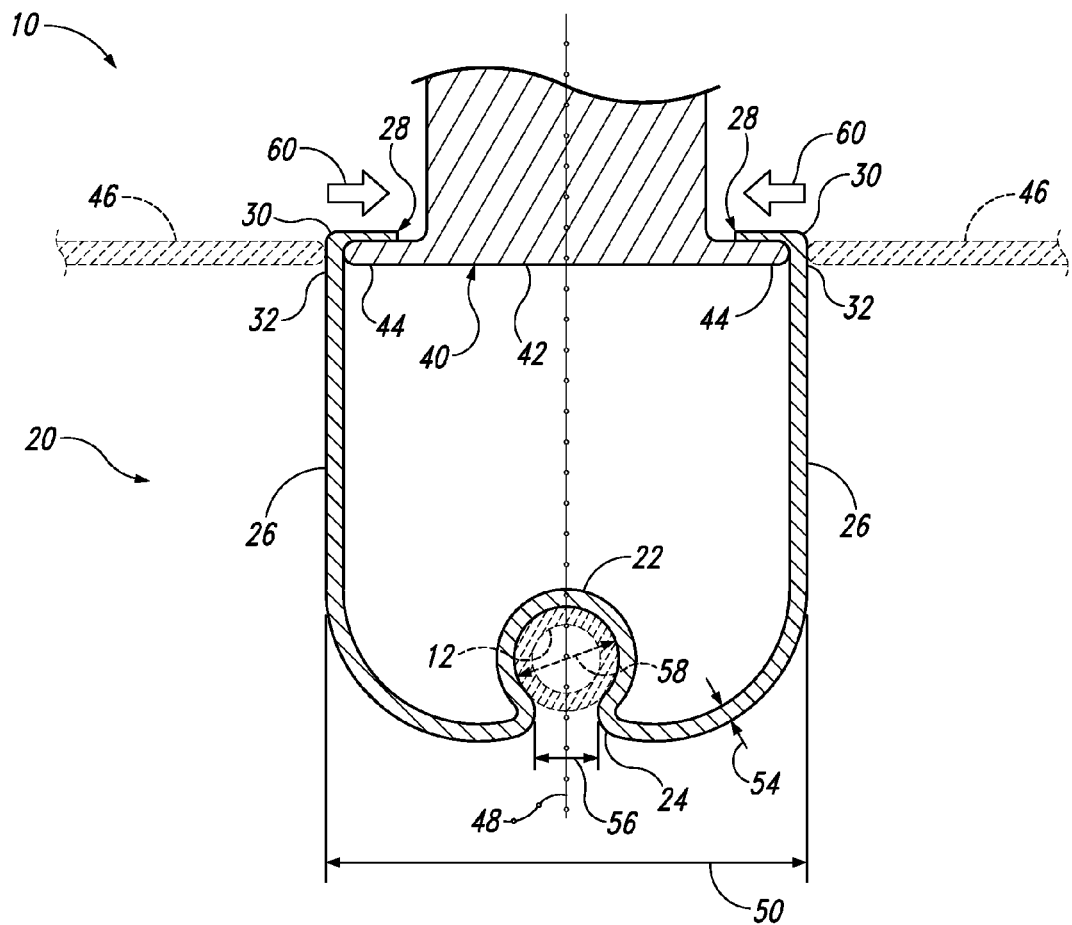
FIG. 5 is a detailed profile of the illustrative, non-exclusive example tube hanger of FIG. 3 when assembled as part of a system for very early smoke detection.

FIG. 5 is a detailed profile of the illustrative, non-exclusive example tube hanger 20 of FIG. 3 when assembled as part of a system 10 for very early smoke detection. The tube hanger 20 is coupled to a support structure 40 which includes a mating support 42 and optional wall panels 46. The suspension arms 26 are laterally flexed causing a grip force 60 to be applied to the mating support 42. The grip force 60 is applied through the support coupling mechanism 28 and/or the coupling elements 30. The tube hanger 20 is configured to hang substantially vertically with the sampling tube 12 retained below the support structure 40. The tube clamp opening 24 is configured to face substantially downward. The coupling elements 30 are configured to rest against mating elements 44 (e.g., lateral flanges) that are part of the mating support 42. Hence, the mechanical interlock between the coupling elements 30 and the mating elements 44 resists downward forces. The tube clamp 22 is configured to flex and release the sampling tube 12 upon application of a sufficient downward force.

Illustrative, non-exclusive examples of inventive subject matter according to the present disclosure are described in the following enumerated paragraphs:

A1. A tube hanger comprising:
a support coupling mechanism;
a tube clamp that defines an opening facing away from the support coupling mechanism; and
a suspension arm spanning between the support coupling mechanism and the tube clamp.

A1.1. A tube hanger for a very early smoke detection system, the tube hanger comprising the tube hanger of paragraph A1.

A2. The tube hanger of any of paragraphs A1-A1.1, wherein the tube hanger is a unitary body.

A2.1. The tube hanger of paragraph A2, wherein the unitary body defines the support coupling mechanism, the tube clamp, and the suspension arm.

A3. The tube hanger of any of paragraphs A1-A2.1, wherein the tube hanger is formed into a band that defines at least one of the support coupling mechanism, the tube clamp, and the suspension arm.

A3.1. The tube hanger of paragraph A3, wherein the band is bent, folded, extruded, stamped, cut, and/or molded to define one or more of the support coupling mechanism, the tube clamp, and the suspension arm.

A3.2. The tube hanger of any of paragraphs A3-A3.1, wherein the band has a substantially uniform thickness.

A3.3. The tube hanger of any of paragraphs A3-A3.2, wherein the band has a thickness less than 20 mm, less than 15 mm, less than 12 mm, less than 10 mm, less than 8 mm, less than 6 mm, less than 4 mm, less than 2 mm, less than 1 mm, 1-20 mm, and/or 2-6 mm.

A4. The tube hanger of any of paragraphs A1-A3.3, wherein the tube hanger has a central axis from a center of the support coupling mechanism to a center of the opening of the tube clamp.

A5. The tube hanger of any of paragraphs A1-A4, wherein the tube hanger includes at least one of a polymer, a plastic, and a metal.

A5.1. The tube hanger of paragraph A5, wherein the tube hanger is essentially composed of a plastic.

A6. The tube hanger of any of paragraphs A1-A5.1, wherein the tube hanger is visually distinct.

A6.1. The tube hanger of paragraph A6, wherein the tube hanger is at least one of distinctly colored, brightly colored, striped, fluorescent, luminescent, and luminous.

A7. The tube hanger of any of paragraphs A1-A6.1, wherein the tube hanger is compact.

A7.1. The tube hanger of paragraph A7, wherein the tube clamp is configured to accept a tube with an outer diameter, wherein the tube hanger has a width less than 5 times the outer diameter, less than 4 times the outer diameter, less than 3 times the outer diameter, less than 2.5 times the outer diameter, less than 2 times the outer diameter, less than 1.5 times the outer diameter, less than 1.2 times the outer diameter, less than 1.1 times the outer diameter, and/or 1.1-5 times the outer diameter.

A7.2. The tube hanger of any of paragraphs A7-A7.1, wherein the tube hanger has a width less than 200 mm, less than 150 mm, less than 100 mm, less than 80 mm, less than 60 mm, less than 50 mm, less than 40 mm, less than 32 mm, less than 28 mm, less than 24 mm, 20-200 mm, and/or 40-100 mm.

A7.3. The tube hanger of any of paragraphs A7-A7.2, wherein the tube hanger has a depth less than 100 mm, less than 80 mm, less than 60 mm, less than 50 mm, less than 40 mm, less than 32 mm, less than 28 mm, less than 24 mm, less than 20 mm, less than 16 mm, less than 12 mm, less than 10 mm, 10-100 mm, and/or 12-40 mm.

A8. The tube hanger of any of paragraphs A1-A7.3, wherein the tube hanger has a substantially uniform depth.

A9. The tube hanger of any of paragraphs A1-A8, wherein the tube hanger comprises at least two suspension arms spanning between the support coupling mechanism and the tube clamp.

A9.1. The tube hanger of paragraph A9, wherein the tube hanger has a central axis, wherein the suspension arms are substantially symmetrically disposed about the central axis.

A10. The tube hanger of any of paragraphs A1-A9.1, wherein the suspension arm/arms has/have an arcuate profile.

A11. The tube hanger of any of paragraphs A1-A10, wherein the suspension arm/arms forms/form an elastic spring between the tube clamp and the support coupling mechanism.

A12. The tube hanger of any of paragraphs A1-A11, wherein the suspension arm/arms is/are flexible.

A13. The tube hanger of any of paragraphs A1-A12, wherein the tube hanger is configured to apply a grip force through the support coupling mechanism.

A14. The tube hanger of any of paragraphs A1-A13, wherein the support coupling mechanism is configured to couple to a mating support.

A14.1. The tube hanger of paragraph A14, wherein the support coupling mechanism is biased to grip the mating support.

A14.2. The tube hanger of any of paragraphs A14-A14.1, wherein the mating support is a portion of at least one of an aircraft, an aircraft interior, and an overhead rail in an aircraft cabin.

A14.3. The tube hanger of any of paragraphs A14-A14.2, wherein the support coupling mechanism is configured for repeated coupling and uncoupling to the mating support.

A14.4. The tube hanger of any of paragraphs A14-A14.3, wherein the mating support includes a lateral flange.

A15. The tube hanger of any of paragraphs A1-A14.4, wherein the support coupling mechanism includes at least one coupling element.

A15.1. The tube hanger of paragraph A15, wherein the at least one coupling element includes at least one of a projection, a hook, a protrusion, a barb, a prong, a stud, a boss, a receptacle, a slot, a socket, and an adhesive.

A15.2. The tube hanger of any of paragraphs A15-A15.1, wherein the at least one coupling element is substantially flat.

A15.3. The tube hanger of any of paragraphs A15-A15.2, wherein the at least one coupling element extends from the suspension arm distal to the tube clamp.

A15.4. The tube hanger of any of paragraphs A15-A15.3, wherein the tube hanger includes at least two suspension arms, wherein each suspension arm includes a coupling element, and optionally wherein each suspension arm includes the same type of coupling element.

A15.5. The tube hanger of any of paragraphs A15-A15.4, wherein the support coupling mechanism includes a plurality of coupling elements and wherein the plurality of coupling elements are configured to cooperate to couple the tube hanger to a mating support.

A15.6. The tube hanger of any of paragraphs A15-A15.5, wherein the tube hanger has a central axis, wherein at least one of the coupling elements faces the central axis, optionally wherein all of the coupling elements face the central axis.

A15.7. The tube hanger of any of paragraphs A15-A15.6, wherein the tube hanger has a central axis, wherein at least one of the coupling elements faces away from the central axis, optionally wherein all of the coupling elements face away from the central axis.

A16. The tube hanger of any of paragraphs A1-A15.7, wherein the tube hanger is configured to retain a tube with the tube clamp.

A16.1. The tube hanger of paragraph A16, wherein the tube has an outer diameter greater than 6 mm, greater than 8 mm, greater than 10 mm, greater than 12 mm, greater than 16 mm, greater than 20 mm, greater than 24 mm, greater than 28 mm, greater than 32 mm, greater than 40 mm, greater than 50 mm, less than 100 mm, less than 80 mm, less than 70 mm, less than 60 mm, less than 50 mm, less than 40 mm, less than 32 mm, less than 28 mm, less than 24 mm, less than 20 mm, 6-100 mm, 6-60 mm, and/or 12-40 mm.

A17. The tube hanger of any of paragraphs A1-A16.1, wherein the tube hanger is configured to accept the/a tube in the tube clamp with a low insertion force, optionally an insertion force of 0-50 N.

A18. The tube hanger of any of paragraphs A1-A17, wherein the tube hanger is configured to accept, without use of tools, the/a tube in the tube clamp.

A19. The tube hanger of any of paragraphs A1-A18, wherein the tube hanger is configured to release the/a tube from the tube clamp upon application of a force directed away from the support coupling mechanism, wherein the force is greater than 20 N (4 lbs.), 30 N (7 lbs.), 40 N (9 lbs.), 50 N (11 lbs.) and/or 60 N (13 lbs.).

A20. The tube hanger of any of paragraphs A1-A19, where the tube hanger is configured to accept and to retain the/a tube after release of the tube due to a force directed away from the support coupling mechanism.

A21. The tube hanger of any of paragraphs A1-A20, wherein the tube clamp is configured to contact the majority of the circumference of the/a tube.

A22. The tube hanger of any of paragraphs A1-A21, wherein the tube clamp has a C-shaped profile.

A23. The tube hanger of any of paragraphs A1-A22, wherein the tube hanger includes two suspension arms, wherein each suspension arm is connected to the tube clamp at a different side of the opening of the tube clamp.

A23.1. The tube hanger of paragraph A23, wherein the tube clamp and the suspension arms form an omegoid profile.

B1. A very early smoke detection system comprising:
a monitoring device;
a sampling tube; and
the tube hanger of any of paragraphs A1-A23.1;
wherein the monitoring device is configured to sample air transported through the sampling tube, and wherein the tube hanger is coupled to a portion of the sampling tube.

B2. The system of paragraph B1, wherein the monitoring device is configured to measure light scattering from air samples.

B3. The system of any of paragraphs B1-B2, wherein the monitoring device is configured to draw air through the sampling tube.

B4. The system of any of paragraphs B1-B3, further comprising:

a suction device configured to draw air through the sampling tube and to transport a portion of the air to the monitoring device.

B5. The system of any of paragraphs B1-B4, wherein the sampling tube includes a sampling inlet, optionally a plurality of sampling inlets.

B6. The system of any of paragraphs B1-B5, further comprising:
a tubing network including the sampling tube.

B7. The system of any of paragraphs B1-B6, wherein the sampling tube is at least one of a pipe, a conduit, a duct, and a hose.

B7.1. The system of paragraph B7, wherein the portion of the sampling tube coupled to the tube hanger is a flexible hose.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required of all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A tube hanger for a very early smoke detection system, the tube hanger comprising:
a support coupling mechanism;
a tube clamp that defines an opening facing away from the support coupling mechanism; and
two suspension arms spanning between the support coupling mechanism and the tube clamp;
wherein each suspension arm is connected to the tube clamp at a different side of the opening of the tube clamp, wherein the tube clamp and the suspension arms form an omegoid profile, wherein each suspension arm includes a projection that is substantially flat and that extends from a tip of the suspension arm distal to the tube clamp, wherein the support coupling mechanism includes the projections of the suspension arms, wherein the tube hanger has a central axis from a center of the support coupling mechanism to a center of the opening of the tube clamp, and wherein both of the projections face the central axis.

2. The tube hanger of claim 1, wherein the tube hanger is a unitary body that is formed into a band that defines the support coupling mechanism, the tube clamp, and the suspension arms.

3. A very early smoke detection system comprising:
a sampling tube; and
the tube hanger of claim 1;
wherein the tube hanger is coupled to a portion of the sampling tube.

4. The tube hanger of claim 1, wherein each suspension arm forms an elastic spring between the tube clamp and the support coupling mechanism.

5. The tube hanger of claim 1, wherein the support coupling mechanism is biased to grip a mating support.

6. The tube hanger of claim 1, wherein the tube hanger is configured to release a tube from the tube clamp upon application of a force directed away from the support coupling mechanism.

7. The system of claim 3, wherein the portion of the sampling tube coupled to the tube hanger is a flexible hose.

8. A tube hanger comprising:
a support coupling mechanism;
a tube clamp that defines an opening facing away from the support coupling mechanism; and
at least two suspension arms spanning between the support coupling mechanism and the tube clamp, wherein each suspension arm is connected to the tube clamp at the opening of the tube clamp and connected to the support coupling mechanism at a tip of the suspension arm distal to the tube clamp;
wherein the tube hanger has a central axis from a center of the support coupling mechanism to a center of the opening of the tube clamp, wherein the suspension arms are substantially symmetrically disposed about the central axis.

9. The tube hanger of claim 8, wherein the tube hanger is a unitary body that defines the support coupling mechanism, the tube clamp, and the suspension arms.

10. The tube hanger of claim 8, wherein the tube hanger is formed into a band that defines the support coupling mechanism, the tube clamp, and the suspension arms.

11. The tube hanger of claim 8, wherein the tube hanger is essentially composed of a plastic.

12. The tube hanger of claim 8, wherein each suspension arm has an arcuate profile.

13. The tube hanger of claim 8, wherein each suspension arm forms an elastic spring between the tube clamp and the support coupling mechanism.

14. The tube hanger of claim 8, wherein the support coupling mechanism is biased to grip a mating support.

15. The tube hanger of claim 14, wherein the mating support is a portion of an aircraft interior.

16. The tube hanger of claim 8, wherein the support coupling mechanism includes a plurality of coupling elements and wherein the plurality of coupling elements are configured to cooperate to couple the tube hanger to a mating support.

17. The tube hanger of claim 8, wherein the tube hanger is configured to release a tube from the tube clamp upon application of a force directed away from the support coupling mechanism.

18. The tube hanger of claim 8, wherein the tube clamp has a C-shaped profile.

19. A very early smoke detection system comprising:
a sampling tube; and
the tube hanger of claim 4;
wherein the tube hanger is coupled to a portion of the sampling tube.

20. The system of claim 19, wherein the portion of the sampling tube coupled to the tube hanger is a flexible hose.

* * * * *